United States Patent
Russell

(10) Patent No.: US 9,642,877 B1
(45) Date of Patent: May 9, 2017

(54) METHOD OF ADMINISTRATION OF CHROMIUM AND MAGNESIUM SULFATE FOR TREATMENT OF ACNE

(71) Applicant: Kenneth O. Russell, Austin, TX (US)

(72) Inventor: Kenneth O. Russell, Austin, TX (US)

( * ) Notice: Subject to any disclaimer, the term of this patent is extended or adjusted under 35 U.S.C. 154(b) by 0 days.

(21) Appl. No.: 15/257,861

(22) Filed: Sep. 6, 2016

Related U.S. Application Data

(60) Provisional application No. 62/275,676, filed on Jan. 6, 2016, provisional application No. 62/277,327, filed on Jan. 11, 2016.

(51) Int. Cl.
*A61K 33/24* (2006.01)
*A61K 33/06* (2006.01)
*A61K 9/00* (2006.01)

(52) U.S. Cl.
CPC ............ *A61K 33/24* (2013.01); *A61K 9/0014* (2013.01); *A61K 33/06* (2013.01)

(58) Field of Classification Search
None
See application file for complete search history.

(56) References Cited

U.S. PATENT DOCUMENTS

| 5,759,559 A * | 6/1998 | Fitzjarrell ............... A61K 8/44 424/401 |
| 5,898,037 A * | 4/1999 | Marx ..................... A61Q 19/08 424/49 |
| 5,962,517 A * | 10/1999 | Murad ................. A61K 31/555 424/417 |
| 6,287,548 B1 * | 9/2001 | Biener ................... A61K 8/19 424/602 |
| 2005/0123620 A1 * | 6/2005 | Chiou ................. A61K 31/555 424/603 |
| 2005/0158404 A1 * | 7/2005 | Goodless .............. A23L 33/105 424/725 |
| 2005/0256200 A1 * | 11/2005 | Burkhart .............. A61K 31/192 514/568 |
| 2006/0193922 A1 * | 8/2006 | Neikrug ............... A61K 31/195 424/563 |
| 2010/0003315 A1 * | 1/2010 | Willeford ............... A61K 33/06 424/450 |
| 2011/0182861 A1 * | 7/2011 | Castiel .................... A61K 8/99 424/93.3 |
| 2016/0367596 A1 * | 12/2016 | Profet .................... A61K 33/08 |

FOREIGN PATENT DOCUMENTS

CA    2637538 A1 * 12/2009

OTHER PUBLICATIONS

CAS Registry No. 10025-73-7 (Nov. 16, 1984).*

* cited by examiner

*Primary Examiner* — Bethany Barham
*Assistant Examiner* — Peter Anthopolos
(74) *Attorney, Agent, or Firm* — Frank Huy Pham; Pham IP Group

(57) ABSTRACT

A method for treatment of acne by applying to human skin a topical composition. The method involves contacting the human skin of area of an afflicted subject with an effective amount of the composition containing chromium and magnesium sulfate, for a period of time sufficient to reduce the redness and blemishes associated with acne. The topical composition is formulated into a pharmaceutically acceptable medium to properly regulate the keratin and sebum production of the skin cells, thereby inhibiting the appearance of acne therefore. The preferred use of the foregoing composition and method is in the treatment of acne.

12 Claims, No Drawings

METHOD OF ADMINISTRATION OF CHROMIUM AND MAGNESIUM SULFATE FOR TREATMENT OF ACNE

CROSS-REFERENCE TO RELATED APPLICATION

The present application is based on, and claims the benefit of priority of U.S. application Ser. No. 62/275,676 filed on Jan. 6, 2016, and 62/277,327 filed on Jan. 11, 2016, the disclosure of which is hereby incorporated by reference herein in its entirety.

BACKGROUND

1. Field of the Invention

The invention relates generally to topical composition and a method for administering pharmaceutical composition to the body skin for treating acne and conditioning skin cells. More particularly, the invention relates to composition and a method for the administration of chromium and magnesium sulfate.

2. Description of the Prior Art

Acne is a skin disease that often scars those afflicted, and can afflict patients at young ages-typically teen years when their self-images are the most sensitive. The scarring is commonly permanent even if the condition is treated with medications. Some patients experience symptoms well into their adult years.

Acne is the name commonly applied to any inflammatory disease of the sebaceous glands, also known as acne vulgaris. The acne vulgaris is a chronic disorder of pilosebaceous units on the face, chest and back.

Acne is believed to be caused typically when the sebaceous glands become clogged due to skin cell debris and an excess of a specific type of skin bacteria. Sebaceous glands are located within the dermis layer of the skin along the hair shaft. Keratin and other chemicals associated with the skin can clog the hair shaft and the sebaceous gland. The bacteria, *Propionibacterium acnes* (*P. acnes*), which is always present, multiplies to a much greater degree when the sebaceous glands are clogged because the bacteria prefer an anaerobic environment, which is present when the glands become clogged.

*P. acnes* produce a lipase enzyme that hydrolyzes triglycerides of the sebaceous gland into free fatty acids. The fatty acids along with bacterial proteins and keratin can irritate the skin tissues. This may lead to an inflammatory response and the formation of an acne lesion.

Acne lesions are caused by a combination of bacteria normally found on the skin, including *propionibacterium acnes* and coagulase-negative staphylococci and micrococci. The lesions are open comedones, which are dilated follicles with central dark, horny plugs. Closed comedones are small follicular papules without inflammatory changes or with inflammatory changes. Superficial pustules are collections of pus, nodules, which are collections of pus deep in the dermis. Large and deep pustular lesions develop from nodules that break down adjacent tissue, enlarge, and form lakes of pus, sinuses and scars.

For example, testosterone stimulates the sebaceous glands accompanying the hair follicles. In response, these glands become enlarged and begin to secrete more sebum than usual. Also, testosterone causes the cells lining a pore to release more keratin, an insoluble protein that is the primary constituent of the hair and the epidermis. Together, the sebum and keratin block a skin pore, resulting in a comedone, also known as a blackhead. Bacteria proliferates in clogged pores, and the body typically responds by releasing enzymes to breakdown the sebum. The enzymes cause the pore to become inflamed. This eventually may result in pustules or pimples. This condition is typically known as acne vulgaris. This response is especially prevalent on the face, back, and shoulders, where a greater amount of sebaceous glands exist.

Free fatty acids and squalene are also known as major lipids that produce sebum. Squalene is highly unsaturated in structure and highly susceptible to peroxidation and photo-degradation. The byproducts, squalene peroxides, promote acne, roughening of skin, and wrinkling. The free fatty acids, when polyunsaturated, degenerate to promote the peroxidation of nearby lipids, including squalene, whereas saturated fats do not.

Various therapeutic methods for treating acne have been attempted including topical antibacterials, e.g. hexachlorophene, and systemic antibiotics such as tetracycline. While the systemic antibiotic treatments are known to be effective, the topical treatments are not highly effective.

For example, Vitamins and herbs often provide more promising results with regard to acne. Vitamin A has proven to be highly effective in treating acne. Since the early seventies, topical retinoic acid or tretinoin, both derivatives of vitamin A, have been used to treat acne topically. These topical agents work by normalizing the skin's production of keratin and the sebaceous glands production of sebum, thereby preventing obstruction of the follicle. Although temporary effective, the benefits of these topical treatments often take several weeks. Also, the patient's condition may become worse before clearing up. Finally, these topical treatments tend to have mild side effects, which include stinging and reddening of the treated areas and possible photosensitivity.

Systemic treatments for acne include the use of oral antibiotics in more serious cases. These treatments are directed towards the reduction in the amount *P. Acnes* in the skin, especially the pilosebaceous structures, and seek to reduce the inflammation caused by waste materials and metabolic bypro ducts from these organisms. Tetracycline antibiotics are most commonly used for this purpose. These include tetracycline, minocycline and doxycycline. Erythromycinis also sometimes used.

In cases where acne does not respond to oral antibiotic treatment, oral isotretinoin is sometimes used. While effective, isotretinoin is also powerfully teratogenic, and women of childbearing age are required to use multiple methods of contraception while taking the drug.

Vehicles such as USP cold cream, ethanol, isopropanol and various creams, ointments, oils, solvents, and emulsions have been used to apply various active ingredients topically. However, these conventional vehicles are not adequate to provide therapeutically effective amounts of antibacterial agents to be retained in the epidermis or to penetrate into the deeper layers of the skin.

Although the above references disclose several methods of treating acne, the treatments often involve adverse side effects, such as overdrying of the skin. Furthermore, the above treatments simply address the acne and fail to condition the skin cells to assist in the treatment and to reduce further incidences of acne.

Accordingly, an effective treatment of acne, particularly its more severe forms, with clinically insignificant side effects is desired.

SUMMARY OF THE INVENTION

The present invention relates to a safe and efficient composition comprising chromium in combination with magnesium sulfate for treatment of acne vulgaris, and provides significant and unexpected benefits for skin, including reducing ambient insulin levels and peroxidation of the sebum, and, inhibiting, reducing, and/or treating appearance, formation, and inflammation of acne on skin, the term "reducing" to be understood to include reducing, inhibiting, treating, delaying, improving, and the like.

The chromium increases the efficiency of the insulin signaling function and consequently reduces the levels of ambient insulin required to optimize the rapid uptake of glucose into all cells, the level of triglycerides produced by the liver and dumped into the blood for the skin cells to transform into sebum, the favorable environment for the bacteria to proliferate, the rate of insulin mediated iron loading into the skin cells, the free radicals that peroxidize the sebum, and supplants iron in the insulin mediated transferring uptake of intracellular iron. Applicant has determined that the lesser bacteria, the lower iron loading on the skin cells from cytokine.

The composition further contains a pharmaceutically acceptable carrier or excipient of magnesium sulfate as a multiplier to accelerate the effective transdermal delivery of chromium. The magnesium component increases the distribution of chromium through the enlarged micro-vessels and into the skin cells.

The composition is transdermally administered to the human skin in a form of lotion, in a fixed-dose of combination, comprising chromium and magnesium sulfate formulated as a topical composition to a patient in need so as to provide a treatment of acne vulgaris, wherein the administration pattern of the composition comprises administering a therapeutically effective amount of the composition for at least 2 weeks, preferably for at least 4 weeks, more preferred for at least 6 weeks.

The composition is administered on a daily basis and preferably twice every day. In another embodiment the composition is administered every two days and preferably once a day. In both cases, the composition is preferably administered in the evening after wash.

The composition comprises at least 0.000422% of chromium III chloride by weight and preferentially comprises 0.00127% to 0.00169% by weight of chromium III chloride relative to the total weight of the composition. The composition comprises also 0.676% to 2.705% by weight of magnesium sulfate, preferably comprises 2.028% to 2.705% by weight of magnesium sulfate relative to the total weight of the composition.

The administration of a composition comprising chromium and magnesium sulfate to a patient sustains its biological response in the treatment of acne vulgaris, wherein the administration pattern of the composition comprises topically applying to the human skin 0.00169% by weight of chromium III chloride and 2.705% by weight of magnesium sulfate twice daily for at least 2 weeks, preferentially for at least 4 weeks, more preferred for at least 6 weeks.

The composition is applied to the human skin which contains both non-inflammatory lesions and inflammatory lesions, and no active nodules or cysts and in preferred embodiment of the composition is a lotion formulation.

The term "pharmaceutically acceptable medium" means a medium that is compatible with the skin, mucous membranes and the integuments.

The term "fixed combination" should be understood as meaning a combination whose active principles are combined at fixed doses in the same vehicle/medium (single formula) that delivers them together to the point of application. Preferably, the pharmaceutical composition in the form of a fixed combination is lotion. In this case, the two active principles are dispersed and intimately mixed, during the manufacture, in the same vehicle, which delivers them together during the application of the lotion.

An embodiment of the present invention further provides vehicles and vehicle components that are especially useful in the transdermal formulations, as well as concentration ranges and processing steps to obtain useful formulation forms including solids, creams, lotions, gels, and liquids.

The present invention further provides objects and advantages that will become apparent from a description of the several embodiments as set forth in the following description.

DETAILED DESCRIPTION OF THE DISCLOSURE

The present invention features a method for the treatment of acne vulgaris by administration of a lotion composition containing chromium. Such product has the following composition:

| Aqueous Lotion (500 g) | |
| --- | --- |
| Chromium III chloride (CrCl3) | 0.204 g |
| Magnesium sulfate | 40 g |
| Mineral oil | 35 g |
| Glyceryl starate | 10 g |
| Propylene glycol | 3 g |

The following details a study that clearly demonstrates the clinical benefit of treatment of acne with chromium III chloride 0.00169%.

The amount of chromium III chloride which may be used in the present invention ranges from about 0.000422 to 0.00169 percent by weight and preferably about 0.676 to 2.705 percent by weight of magnesium sulfate of the composition.

Chromium and magnesium sulfate are available commercially and are made by a number of methods known to those of skill in the art.

Methods and compositions for topical administration of chromium III chloride and magnesium sulfate can successfully treat patients with acne vulgaris. Additionally, chromium and magnesium compounds can be incorporated into solution, lotion, cream, ointment and gel formulations for application to the skin of patients with severe acne. In such topical formulations, concentrations from 0.000422% to 0.00169% by weight of chromium III chloride and 0.676% to 2.705% by weight of magnesium are incorporated into vehicle suitable for application to the skin. The resulting formulations are applied to the skin of acne patients from 1 to 3 times daily.

Example 1

A clinical study of human subjects with acne vulgaris was carried out to show the effectiveness of the composition of the present invention in the treatment of acne. A fixed dose combination of lotion formulations containing chromium III chloride 0.000422% to 0.001695% by weight/total composition weight.

Compositions containing 0.5 mg by weight of chromium III chloride are administered at least once daily for 2 weeks to patients with acne vulgaris. At the end of the 2-week treatment period most patients will demonstrate a significant decrease in the activity of their inflammatory acne lesions.

Formulations A, B, C and D (Table 1) were applied to each subject twice daily. Clinical appraisal was carried out at biweekly intervals.

TABLE 1

| Ingredient | % | | | |
|---|---|---|---|---|
| | A | B | C | D |
| Chromium III chloride | 0.000422 | 0.000844 | 0.00127 | 0.00169 |
| Magnesium | — | 1.352 | 2.028 | 2.705 |

The results of the study are shown in Table 2 below:

TABLE 2

Clinical Evaluation of Acne Treatment

| Formulation | Evaluation Time (Weeks) | | | |
|---|---|---|---|---|
| | 1 | 2 | 4 | 6 |
| A | 0 | 2 | 2 | 3 |
| B | 1 | 2 | 3 | 4 |
| C | 2 | 3 | 4 | 4 |
| D | 2 | 4 | 4 | 4 |

0 = no response
1 = slight improvement
2 = good improvement
3 = very good improvement
4 = dramatic improvement The results of the foregoing tests show that chromium used in the systemic treatment of acne (formulation A) is essentially ineffective as is the vehicle alone. However, the results of the foregoing tests shown a good improvement with magnesium sulfate (formulation B, C, and D).

Example 2

The study of Example 1 is repeated to show the efficacy and safety of the composition of the present invention in the treatment of acne (Table 3). Safety and tolerability were assessed through evaluations of local tolerability and adverse events. At each visit, the investigator rated erythema, scaling, dryness, stinging/burning on a scale.

The efficacy variables were percent lesion count reduction from baseline (total, inflammatory, and non-inflammatory) and subject's assessment of acne on a scale from 0 (marked improvement) to 5 (worse).

The study conducted efficacy evaluations consisting of non-inflammatory lesion counts (open and closed comedones) and inflammatory lesion counts (papules and pustules) and nodules/cysts. Table 3 is a flow chart of assessed measurements during this study.

TABLE 3

| | |
|---|---|
| 1 | Marked Improvement |
| 2 | Moderated Improvement |
| 3 | Minimal Improvement |
| 4 | No Change |
| 5 | Worse |

Local tolerability measures of the signs and symptoms of skin irritation were considered adverse effects only if the severity of the expected signs and symptoms was such that an interruption of the subject's participation in the study, at his/her request or at the investigator's discretion, had occurred. Altered dosing regimens (such as every other day dosing) to manage irritation were not considered to be an interruption of the subject's participation in the study.

The results of the study are shown in Table 4 below.

TABLE 4

Efficacy and Safety Measurements

Efficacy

| Formulation | Evaluation Time (Weeks) | | | |
|---|---|---|---|---|
| | 1 | 2 | 4 | 6 |
| A | 4 | 3 | 3 | 2 |
| B | 3 | 3 | 2 | 1 |
| C | 3 | 2 | 1 | 1 |
| D | 3 | 2 | 1 | 1 |

Safety

| Formulation | Evaluation Time (Weeks) | | | |
|---|---|---|---|---|
| | 1 | 2 | 4 | 6 |
| A | 4 | 3 | 3 | 2 |
| B | 3 | 3 | 2 | 2 |
| C | 3 | 2 | 1 | 1 |
| D | 2 | 1 | 1 | 1 |

As this was an open-label study, only descriptive data presentations were made. No formal statistical hypotheses were tested. Descriptive statistics were used to summarize all data.

Treatment with chromium, 0.00169 for up to 4 weeks showed continuing improvement in lesion counts (non-inflammatory, inflammatory and total) starting week 4. The greatest reductions in lesion counts were seen after 6 weeks of treatment.

Overall improvement was observed in the subject's assessment of acne. The median assessment was "Moderated Improvement" at week 2, and "Marked Improvement" at week 4

In conclusion, chromium III chloride, 0.00169% was well-tolerated and effective in treatment of acne vulgaris patients. Signs and symtomps of skin irritation (erythema, dryness, scaling, and stinging/burning) were mostly mild or moderate and were transient.

Safety findings were consistent with the known profile of chromium. No unexpected, either systemic or dermatological, evidence of cumulative toxicity was observed over time. Consequently, extending treatment beyond 6 weeks does not suggest substantial additional risk for the subjects treated with chromium III chloride 0.000169%.

The efficacy of chromium III chloride 0.000169% was demonstrated for non inflammatory, inflammatory and total lesions. Chromium III chloride 0.000169% showed continuing reductions greater than 95% in all lesion counts for subjects treated for 6 weeks.

Invention and its practical application to persons who are skilled in the art. As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting. Thus, the breadth and scope of the present invention should not be limited by any of the above described exemplary embodiments, but should be defined only in accordance with the following claims appended hereto and their equivalents.

Having illustrated and described the principles of the present invention in a preferred embodiment, it will be apparent to those skilled in the art that the embodiment can be modified in arrangement and detail without departing from such principles. Any and all such embodiments are intended to be included within the scope of the following claims.

What is claimed is:

1. A method for treating acne in a human in need thereof comprising topically administering to an area of skin a composition comprising 0.000422% to 0.00169% by weight of chromium(III) chloride and 0.676% to 2.705% by weight of magnesium sulfate wherein said area of skin is selected from the group consisting of (1) an area of skin having a non-inflammatory lesion, (2) an area of skin having an inflammatory lesion, and (3) an area of skin having no active nodule or cyst.

2. The method of claim 1, comprising topically administering said composition for at least two (2) weeks.

3. The method of claim 1, comprising topically administering said composition for at least four (4) weeks.

4. The method of claim 1, comprising topically administering said composition for at least six (6) weeks.

5. The method of claim 1, comprising topically administering said composition at least once every day.

6. The method of claim 1, comprising topically administering said composition in the evening after washing said area of skin.

7. The method of claim 1, wherein said composition is a lotion.

8. The method of claim 1, wherein said composition is a gel.

9. The method of claim 1, wherein said composition comprises 0.000422% by weight of chromium(III) chloride and 0.676% by weight of magnesium sulfate.

10. The method of claim 1, wherein said area of skin is selected from the group consisting of (1) an area of skin having a non-inflammatory lesion and (2) an area of skin having an inflammatory lesion.

11. The method of claim 1, wherein said acne is selected from the group consisting of acne vulgaris, acne conglobata, acne fulminans, pyoderma facaile, acne keloidalis, chloracne, and steroid acne.

12. The method of claim 1, wherein (1) said composition is in a form selected from the group consisting of solid, cream, lotion, gel, and liquid; and (2) said composition exerts a transdermal effect following said topical administration.

* * * * *